United States Patent [19]
Dagenais et al.

[11] Patent Number: 5,354,575
[45] Date of Patent: Oct. 11, 1994

[54] ELLIPSOMETRIC APPROACH TO ANTI-REFLECTION COATINGS OF SEMICONDUCTOR LASER AMPLIFIERS

[75] Inventors: Mario Dagenais, Chevy-Chase; I-Fan Wu, Hyattsville, both of Md.

[73] Assignee: University of Maryland, College Park, Md.

[21] Appl. No.: 47,840

[22] Filed: Apr. 16, 1993

[51] Int. Cl.$^5$ ............. B05D 3/06; B05D 5/06; C23C 16/00; C23C 14/00
[52] U.S. Cl. ............. 427/10; 427/567; 427/8; 427/162; 427/164; 427/255.1; 427/163.4; 204/192.13
[58] Field of Search ............. 427/8, 9, 10, 561, 566, 427/567, 582, 583, 584, 585, 586, 595, 596, 255, 255.1, 255.2, 255.3, 162, 163, 164, 165, 167; 204/192.1, 192.12, 192.13, 192.14, 192.15, 192.22, 192.23, 192.26, 192.27, 192.28, 192.29; 359/333–349; 250/225

[56] References Cited

U.S. PATENT DOCUMENTS

| | | | |
|---|---|---|---|
| 4,332,833 | 6/1982 | Aspnes et al. | 427/10 |
| 4,434,025 | 2/1984 | Robillard | 156/601 |
| 4,647,207 | 3/1987 | Björk et al. | 356/369 |
| 4,708,884 | 11/1987 | Chandross et al. | 427/255.3 |
| 4,770,895 | 9/1988 | Hartley | 427/523 |
| 4,778,251 | 10/1988 | Hall et al. | 427/166 |
| 4,792,463 | 12/1988 | Okada et al. | 427/255.3 |
| 4,906,844 | 3/1990 | Hall | 250/225 |
| 4,934,788 | 6/1990 | Southwell | 350/164 |
| 4,970,120 | 11/1990 | Laschewsky et al. | 427/164 |
| 5,009,485 | 4/1991 | Hall | 427/255.2 |
| 5,009,920 | 4/1991 | Lee | 427/255.2 |
| 5,034,277 | 7/1991 | Laschewsky et al. | 427/164 |
| 5,091,320 | 2/1992 | Aspnes et al. | 437/8 |
| 5,131,752 | 7/1992 | Yu et al. | 427/10 |
| 5,160,576 | 11/1992 | Robbins | 204/192.33 |

OTHER PUBLICATIONS

R. W. Collins, "Review Article: Automatic rotating element ellipsometers: Calibration, operation, and real-time applications", *Rev. Sci. Instrum.* vol. 61, #8, Aug. 1990 pp. 2029–2062.

Wu et al., "Real Time In Situ Monitoring of Anti-Reflection Coatings Of Semiconductor Laser Amplifiers by Ellipsometry" LEOS, Nov. 1991.

*Primary Examiner*—Marianne Padgett
*Attorney, Agent, or Firm*—Christopher N. Sears

[57] ABSTRACT

The invention describes a real-time in situ ellipsometric monitoring and control system using an ellipsometer to control the averaged refractive index of the deposited film during the AR coating of semiconductor laser diode facets for laser amplifiers and superluminescent LED. The input and output window birefringences are taken into account and calibrated the windows mounted on the vacuum chamber to include the effects of the pressure and mounting stress. In addition to the conventional four-medium model which gives an averaged refractive index, an adaptive multilayer model which takes into account an increasing number of layers as the evaporation proceeded is developed to monitor the instantaneous changes of the refractive index. Each ellipsometric measurement lasts only 0.5s and provides two sets of refractive index and thickness data as derived by the two multilayer models. Both measured data are used for the refractive index control to achieve a good feedback response. This fast and sensitive measurement technique makes possible the feedback control of the refractive index in real time which in turn allows for better control of the deposition condition and also improves the reproducibility of the AR coating process. By combining the two measured refractive indices and using the weighted average as the control factor, precise control of the average refractive index within ±0.01 can be achieved and traveling-wave semiconductor laser amplifiers and superluminescent LEDs with facet reflectivities of order $10^{-5}$ or less are obtained reproducibly for a single layer coating. Multilayer AR coatings can also be fabricated by using the invention technique with different combination of materials. The coatings can further be fine tuned by using wet etching or an ion gun mounted in the same deposition chamber for film thinning.

19 Claims, 15 Drawing Sheets

After Photoresist Application:

ELLIPSOMETRIC APPROACH TO ANTI-REFLECTION COATINGS OF SEMICONDUCTOR LASER AMPLIFIERS

FIELD OF INVENTION

The U.S. Government has the rights to this invention pursuit to grants provided by NSF (contract number: ECS-8818797), DARPA (contract number: DAAH01-89-C-0067), RADC (contract number: F19628-S9-K-0036), and NSA (contract number: MDA 904-92-(6003)). The invention relates to a method of making anti-reflection coatings of semiconductor laser amplifiers and superluminescent light emitting diodes (LEDs) using real-time ellipsometry techniques and apparatus.

BACKGROUND OF INVENTION

Traveling-wave semiconductor laser amplifiers (TWSLAs) will find applications as optical preamplifiers in high sensitivity receivers, as signal boosters for interprocessor optical interconnects, in local area networks, and photonic switching systems. Because of their very large bandwidth (~10 THz), they might also play an important role in future high capacity wavelength division multiplexed systems. The superluminescent LED is the key element in several applications such as a tunable external cavity semiconductor laser which provides a tunable, stable, and ultra-narrow linewidth(less than 100kHz) laser source, and for optical intensity enhancement using high Q optical cavity. An ultra-low AR coating further provide the features of high gain and high power for both devices since the cavity resonances can be suppressed under high injection current. Both arc typically fabricated by depositing anti-reflection (AR)coatings on both facets (for laser amplifiers)or single facet (for superluminescent LED) of a laser so as to suppress the Fabry-Perot transmission peaks originating from the laser cavity. Obtaining ultra-low facet reflectivity is of utmost importance in all of these promising applications. For example, in order to make a 25 dB gain with less than 1 dB spectral gain ripple for a laser amplifier, a facet reflectivity of $10^{-4}$ or less is required. Similar requirement is needed for the applications which utilize superluminescent LEDs as an element, such as the tunable external cavity laser where continuous spectral tuning and low spectral ripple are needed. This implies that the reactive index and the thickness of the AR coating have to be controlled to within $\pm 0.02$ and $\pm 20$ Å, respectively. Therefore, the controlled deposition of an appropriate coating material with a precise refractive index and thickness is required for obtaining high performance traveling-wave laser amplifiers and superluminescent LEDs.

The refractive index control can be achieved by using SiO, one of the most widely used material for this type of deposition. The adjustments of the refractive index of SiO is usually done by adjusting the oxygen pressure in the deposition chamber. A non-stoichiometric film composition is then obtained which is represented by $SiO_x$, where x can vary between 1 and 2 as the refractive index is adjusted between 1.9 and 1.45, respectively. In addition to the oxygen pressure, the deposition rate is another important factor which can significantly affect the final value of the refractive index. Because the refractive index depends not only on the oxygen pressure but also on the deposition rate, it has generally been difficult to obtain the same refractive index from run to run lot reproducible low facet reflectivity manufacturing.

Several in situ monitoring techniques have been used for the AR coatings of semiconductor lasers. They include the monitoring of the output light power vs. bias current (see the article entitled "Directly controlled deposition of anti-reflection coatings for semiconductor lasers," by M. Serenyi and H. U. Habermeier, published in Applied Optics, volume 26, 1987 at pages 845–849), the measurement of the facet loss induced forward voltage changes (see the article entitled "In situ reflectivity monitoring of anti-reflection coatings on semiconductor laser facets through facet loss induced forward voltage changes," by J. Landreau and H. Nakajima, *Appl. Phys. Lett.*, published in Applied Optics volume 56, 1990 at pages 2376–2378), and the measurement of the spontaneous emission spectrum. However, none of these techniques monitors in real time the refractive index of the film. Typically, the refractive index is only measured after deposition and its value suffers from variations from run to run. In order to reproducibly obtain a film with a given refractive index, a technique capable of accurately measuring the refractive index of the film during the deposition is needed. The invention herein uses real-time in situ ellipsometry for the refractive index measurement, which permits accurate, fast, and non-destructive measurements of the film characteristics during the deposition. In situ ellipsometry is a technique that has also been widely used in many other applications for real-time monitoring, see the technical review article by R. W. Collins entitled "Automatic rotating element ellipsometers: calibration, operation, and real-time applications," published in Rev. Scient. Instru., volume 61, 1990, pages 2029–2062. In some applications, it is used for process control, such as Yu et al. U.S. Pat. 5,131,752 and Aspnes et al. U.S. Pat. No. 5,091,320. However, most of tile real time applications as taught and suggested require monitoring the ellipsometric data with ($\Delta$, $\psi$) coordinate, and do not extract the refractive index and thickness of the measured film from $\Delta$ and $\psi$ in real time. This is also the case in Yu's U.S. Pat. No. 752 for endpoint control of a film deposition or etching.

In Aspnos' U.S. Pat. No. '320, a general idea of using the extracted dielectric function and thickness from the $\Delta$ and $\psi$ to control a material growth is taught. However, the invention only demonstrates a method of extracting the dielectric function using an approximation that the dielectric function of the deposited film is sufficiently close to the substrate such that the reflection from the interface between the film and the substrate can be neglected. In practice, for the case of depositing a non-absorptive dielectric film on a semiconductor substrate, the above approximation is not valid. The exact solution has to be solved numerically. Therefore, a substantial computation power is previously considered necessary. The invention herein further demonstrates that for the case of non-absorptive films, the required computation can be implemented on a personal computer with a total measurement time in about half a second which allows for real-time monitoring and deposition control.

In the teaching by I-Fan Wu et al. entitled "Real-time "in situ monitoring of antireflection coatings of semiconductor laser amplifiers by ellipsometry," presented in IEEE Lasers and Electro-Optics Society (LEOS) Annual Meeting, November, 1991, a general approach to the AR coating by using ellipsometry is disclosed. However, this teaching does not provide critical information of the required methodology for the refractive index extraction and control schemes for better reproducibility of AR coating for semiconductor lasers with a lower facet reflectivity in the range of $10^{-5}$ or less.

SUMMARY OF INVENTION

The invention's method of making AR coatings for laser amplifiers and superluminescent LEDs uses an ellipsometer mounted on a deposition chamber where a dedicated personal computer is used for data acquisition, analysis, and refractive index control.

It is an object of the invention to measure the refractive index of a transparent dielectric film on a reference substrate using real-time ellipsometry without making approximation in the extraction of the reactive index and the film thickness, and to use the measured data for controlling the refractive index of the film. An algorithm for an adaptive multilayer model is used to extract the refractive index of the coated film, and a real-time feedback control for the refractive index adjustment is implemented.

Another object of the invention is a procedure for in situ calibrating the incident angle of the ellipsometer at the beginning of each deposition. The procedure is based on the well known refractive index of a semiconductor material (such as GaAs or Si) with a fresh surface. This calibration procedure reduces the possible deviation of the incident angle due to realignment of the sample holder for each run that improves the accuracy of the ellipsometric measurement.

Still another object of the invention is an ellipsometric approach which can also be applied to a multilayer AR coating system. Different combinations of layer structures are possible. The ellipsometric measurements provide accurate information for each layer so that high reproducibility is achievable.

Still another object of the invention is that the the index control technique for a single layer AR coating can be used in a multilayer system to obtain a special design of the AR coatings. For example, in a double-layer system, the first layer (next to the substrate) can be index controlled using a nonstoichiometric material to obtain a specific index value with a proper thickness so that the second layer can be a stable, stoichiometric material which acts like a passivation layer for the first layer, while the reactive index of the second layer has a large tolerance to allow variations of deposition parameters.

Yet, still another object of the invention is that an AR coating can be fine tuned to achieve the most desirable characteristics by utilizing the following techniques: the in situ ellipsometry, in situ ion milling with an ion gun mounted in the deposition chamber, the reflectivity measurement technique, and any wet etching technique.

BRIEF DESCRIPTION OF THE DRAWINGS

FIG. 8 shows a typical record of a deposition.

DETAILED DESCRIPTION

Figure 1:
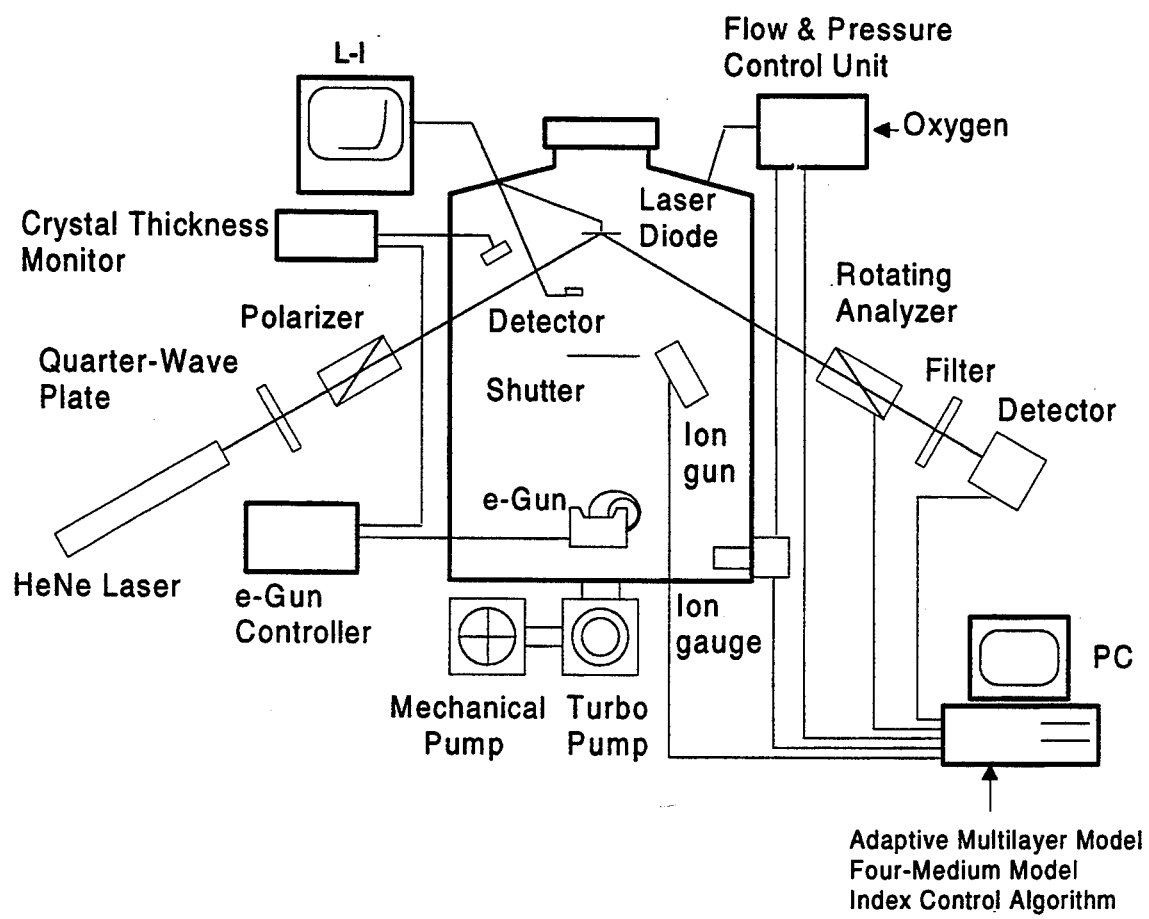
FIG. 1 shows the schematic of the experimental setup.

As an example of demonstrating the invention, FIG. 1 shows a typical experimental setup. A rotating-analyzer ellipsometer (RAE) is attached to an electron beam deposition chamber which is pumped down by a turbo-molecular pump. Different configurations of the ellipsometers and the pumping system are possible for employing the current invention. The sample holder is mounted on a high-vacuum micropositioner with 5 degrees of freedom (X, Y, Z, rotation, and tilt) to adjust the position and orientation of the sample. A linearly polarized HeNe laser is used as the light source. The light beam is expanded and then focused on the sample surface at an proselected incidence angle in the range from 0 to 90 degree. 60° is chosen in this demonstrating example. In principle, the ellipsometric measurements can be directly done on the laser facet, but, in practice, because of mechanical vibration from the vacuum pumps and the shutter movement during deposition, the real-time monitoring is performed on a small reference substrate which could be the cleaving facet of the laser to be coated or a reference substrate about 1 to 2 away from the laser.

On the input side(the polarizer arm), a quarter-wave plate changes the linearly polarized light to a circularly polarized beam before the polarizer so that the intensity stays about constant while the azimuth angle of the polarizer is adjusted. On the output side(the analyzer arm), the reflected light is modulated by the rotating analyzer and detected by a silicon photodiode. Before it reaches the detector, a narrow-band optical filter is inserted in the light path to reject any unwanted background radiation.

An optical shaft encoder is attached to the rotating analyzer which is driven by a synchronous motor. The rotation speed of the analyzer is about 650 rpm in this example. Other rotation speeds are possible depending on the system design. The shaft encoder has two output channels connected to the timing inputs of tile A/D converter: the index channel with one pulse per revolution triggers the data acquisition for a measurement, while the incremental channel sends out 1024 pulses per revolution to clock the A/D conversions. The detected signal from the photodetector is amplified and adjusted to fit the input range of the 12-bit A/D converter. The sampled data are then processed to extract the values of the refractive index and the thickness of the deposited film.

A. Alignment and Calibration

The alignment of the polarizer azimuth on the input side is based on the principle that the polarization of a linearly polarized light is unchanged after reflection from a smooth surface if and only if its polarization is perfectly parallel or perpendicular to the plane of incidence. A null intensity is detected by adjusting both the polarizer and analyzer in such a way that the polarization of the incident light is parallel or perpendicular to the plane of incidence while the azimuth of the analyzer is chosen to be orthogonal to that of tile light. The sensitivity of the photodetector is increased to improve the accuracy of this measurement. The accuracy with which the polarizer azimuth can be set is determined to be about ±0.020 based on repeated realignments. The values of the analyzer azimuth and the amplitude response of the electronic circuit to the AC component of the detected signal are obtained by a similar approach to the one described in the technical article by D. E. Aspnes and A. A. Studna entitled "High precision scanning ellipsometer," published at Applied Optics, volume 14, 1975, pages 220–228. A precision of 0.01° for the analyzer azimuth and 0.0005 for the AC amplitude response (normalized to that of the DC response) is obtained. These measurement are carried out with the windows unmounted.

Figure 2:
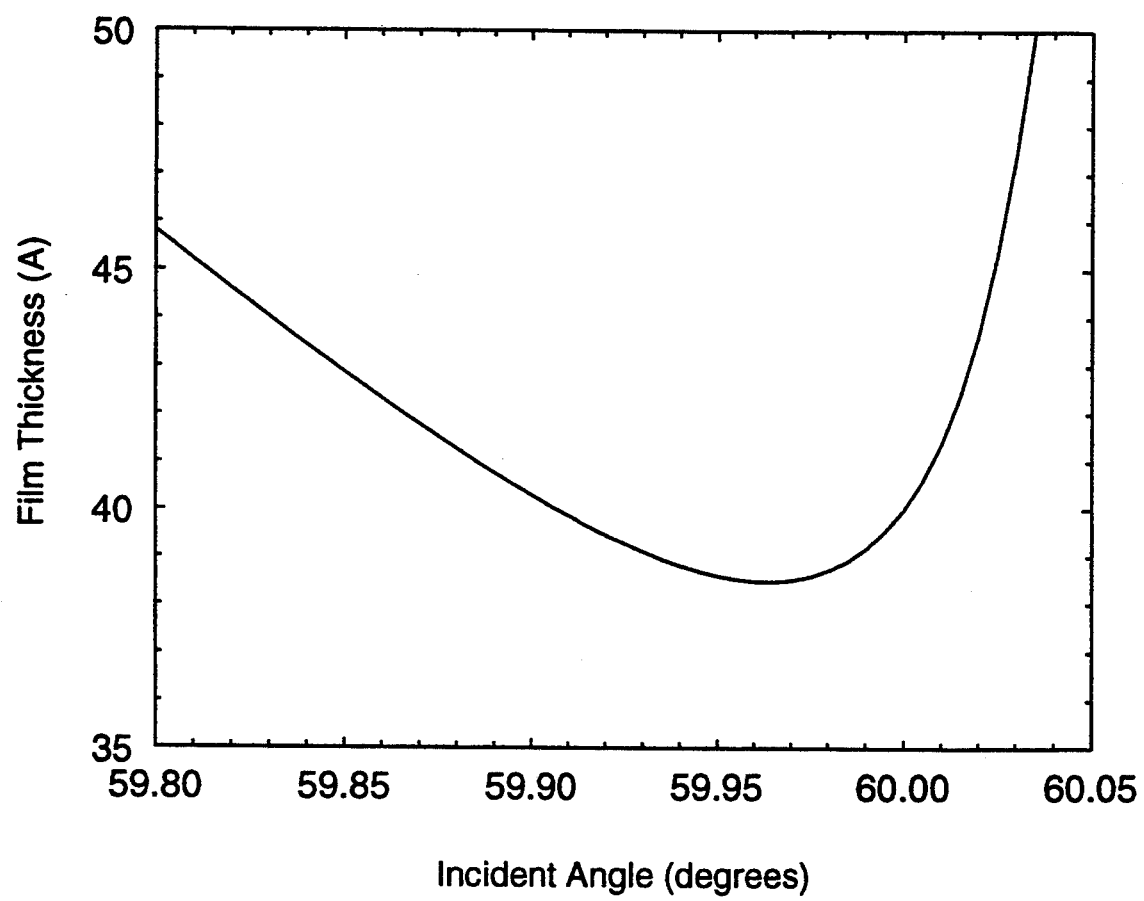
FIG. 2 shows the relation between the extracted overlayer thickness and the assumed incident angle.

The incidence angle of the ellipsometer is set at around 60° at the time the optical ports for the windows are welded on the chamber. This angle is originally chosen to minimize the error on the ellipsometer parameter extractions. After each loading of a sample, the sample holder has to be repositioned and the incident angle has to be realigned. A small variation of the incident angle may occur for each alignment. A procedure to calibrate the incident angle after each sample loading is therefore developed. It is based on the assumption that the reference sample has a well known refractive index, such as GaAs and Si, and that only a thin (less than 100 Å) overlayer exists on the reference sample. For a given pair of measured ellipsometric angles ($\Delta$ and $\psi$) from such a surface, the extracted thickness of the overlayer can be obtained as a function of the incident angle by using a three-medium model. A simulation is shown in FIG. 2, where a 40 Å overlayer with a refractive index 1.7 on a GaAs substrate and a 60 degree incident angle are assumed. Note that the thickness of the overlayer can be minimized over the incident angle. The minimum thickness and the corresponding incident angle are within 2 Å and 0.04° from the true thickness and the true incident angle, respectively. Hence, this method provide the tool to in situ calibrate the incident angle at the beginning of each run.

B. Window Effects

The major source of error in in situ ellipsometry comes from the input and output windows on the vacuum chamber which introduce a small change of the polarization states due to stray birefringence. This birefringence is caused by tile intrinsic stress in the window or from the mounting of the windows on the vacuum chamber. In order to account for the window birefringence, the windows are modeled as small-retardation wave plates.

The detected light intensity at tile output of a rotating-analyzer ellipsometer is given by $$I(A) = I_0(1 + a\cos 2A + b \sin 2A), \quad (1)$$

where $I_0$ is the dc component, (a, b) are the normalized Fourier coefficients, and A is the azimuth of the analyzer referred to the plane of incidence. The effects of the windows can be expressed in terms of the errors in the measured quantities (a, b), as has been discussed in several technical articles, such as the one published by J. M. M. de Nijs and A. van Silfhout entitled "Systematic and random errors in rotating-analyzer ellipsometry," published in Journal of Optical Society of America A, volume 5, 1988, pages 773–781. Having taken into account the window errors, the measured Fourier coefficients can be written as $$a = \frac{\tan^2\psi - \tan^2 P + u\tan\psi\sin\Delta}{\tan^2\psi + \tan^2 P}, \quad (2)$$

$$b = \frac{2\tan\psi\tan P\cos\Delta + v\tan\psi\sin\Delta}{\tan^2\psi + \tan^2 P}, \quad (3)$$

where $\psi$ and $\Delta$ are the ellipsometric angles defined by where $r_p$ and $r_s$ are the Fresnel reflection coefficients of the sample surface for the polarization parallel (p) and perpendicular (s) to the plane of incidence, respectively. The coefficients u and v in Eqs. 2 and 3 are given by $$u = 2Y_o \sin 2\phi_o \tan P, \quad (5)$$

$$v = \sin 2\phi_i(1-\tan^2 P) - 2) x(Y_i\cos 2\phi\Delta_i + Y_o\cos 2\phi\Delta_o) \tan P, \quad (6)$$

where P and tan P are defined as the angle its trigonometric value respectively of the azimuth angle, measured counterclockwise with respect to the plane of incidence when viewed against the direction of propagation of light, and Y's are the retardations and azimuths of the optical axes for the input and the output windows, respectively, with the subscripts i and o denoting the input and the output windows. Since a small retardation is assumed for the window, i.e., $Y \ll 1$, only the first order terms are considered in the above error analysis. However, this approximation can not be applied if the trigonometric terms involving $\Delta$ and $\psi$ are small and comparable to the neglected high-order terms.

In a first order approximation, it can be noted that the coefficients u and v given in Eqs. 5 and 6 are only functions of the input and the output windows and the polarizer azimuth, and not dependent on the sample parameters. Instead of using a separate, straight-through setup to measure the individual Y's and $\psi$'s of each window and assuming that all parameters are unchanged after mounting the windows on the chamber, the optical parameters of the windows can all be lumped into u and v, as described in the following paragraph. In this way any change of the window parameters after mounting to the deposition chamber due to residual stress or any pressure difference between the inside and the outside of the chamber can be easily included. The loading of the sample and of the evaporation material in the e-gun is done through separate vacuum ports and therefore does not affect the built-up strain in the windows of the RAE.

Figure 3:
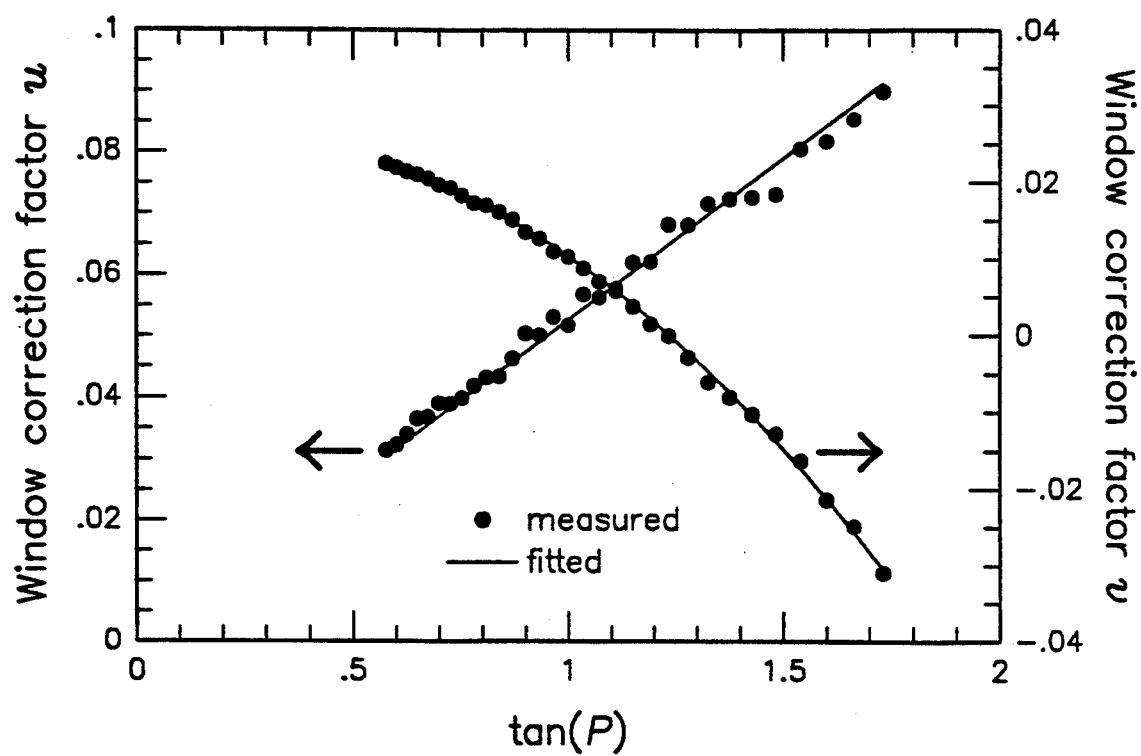
FIG. 3 shows the window correction factors u and v as functions of tan P.

To calibrate the window errors, a sample is placed on the sample holder, and Y and Δ are measured with the windows unmounted. After tile windows are mounted to the chamber and the chamber is pumped down, the Fourier coefficients a and b are measured at a given polarizer azimuth. Then u and v are solved for the given polarizer azimuth from Eqs. 2 and 3 using the ψ and Δ previously measured without windows. The validity of the small retardation wave plate model for both windows is verified by fitting the values of u and v to tan P, where u is proportional to tan P and v is a second order polynomial of tan P with only two parameters. By measuring the Fourier coefficients at different polarizer azimuths, the curves of u and vs. tan P are obtained. FIG. 3 shows the typical results, where a $SiO_2/Si$ sample is measured. The solid dots are measured values and the lines are the fitted curves. The results show a very good agreement with the model.

C. Data Reduction and Film Models

The invention herein is primarily for the deposition of a transparent film over the wavelength range of interest. The special numerical method for solving the film parameters of a transparent film is proposed by Chariot et al., see the technical article by D. Charlot and A. Maruani entitled "Ellipsometric data processing: an efficient method and an analysis of the relative errors," published in *Applied Optics*, volume 24, 1985, page 3368–3373. Since a short measuring time is desired, only one-zone measurement is performed with the azimuth of the polarizer set at 45°.

Figure 4A:
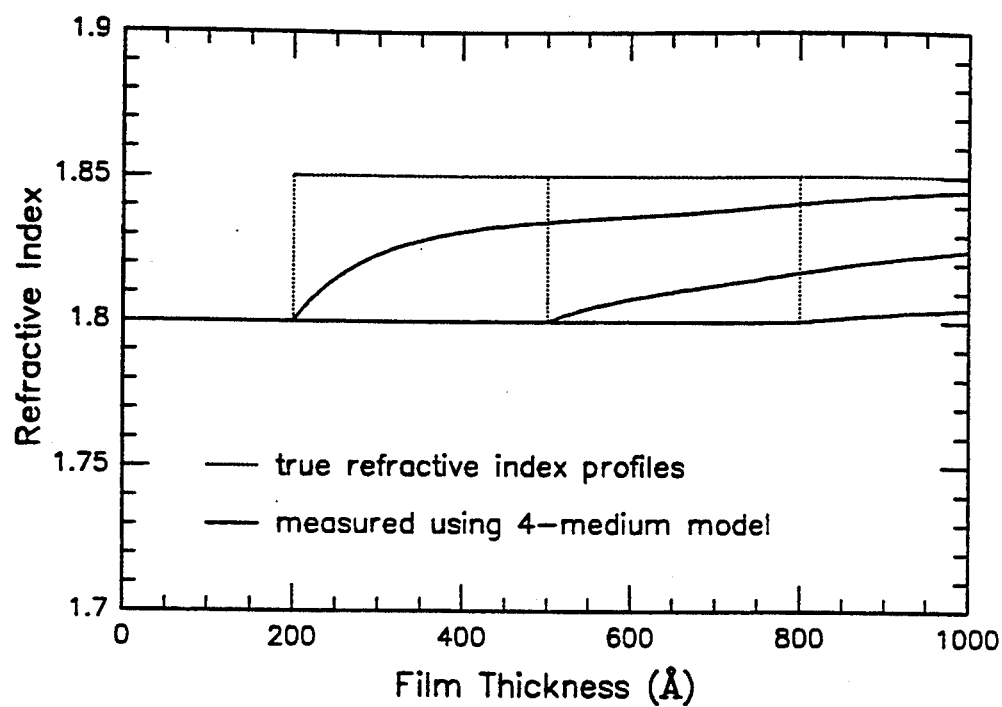
FIG. 4 shows the response of the ellipsometric measurement to a refractive index change from 1.80 to 1.85 at an overall layer thickness of 200, 400, and 600Å by FIG. 4(a) the four-medium model and FIG. 4(b) the adaptive multilayer model.

The refractive index and thickness derived from an ellipsometric measurement are usually based on a four-medium model including an overlayer. However, this model only gives an averaged refractive index over the entire thickness of the deposited film. As the refractive index of the deposited film change during coating following a deliberate change of the deposition conditions by the refractive index control process or following some unwanted and random perturbations, the sensitivity of this four-medium model to refractive index changes will decrease as the film thickness increases. FIG. 4a shows a simulation of the response of the measurement system based on the four-medium model to a step change of the refractive index from 1.80 to 1.85 at different thicknesses on a CaAs substrate. The refractive index of the overlayer is assumed to be 1.80. The dotted lines represent the real refractive index profiles, while the solid ones are the extracted response based on a four-medium model. It can be observed that the measured refractive index can not follow the change of the refractive index, and the response becomes worse as the thickness increase. A more sensitive approach to extracting the instantaneous refractive index of the newly deposited film is clearly desirable. Aspnes et al. has recently proposed an approximate method for extracting the local dielectric function during the growth of $Al_xGa_{1-x}$. As using a first-order expansion of the Fresnel reflectance equation. However, this approach is only valid in the case where the dielectric functions of the substrate and the film are sufficiently similar so that the reflectance contribution at the interface can be neglected. For the case in this invention, the solution has to be obtained using the proper model, without making any approximation.

Since the ellipsometric measurement is intended to start with a film-free surface, and since all the measured data are recorded along with the deposition, the model of the film structure can be updated by using the recorded information to accommodate the changing parameters of the film. Therefore, the invention herein uses a real-time algorithm with an adaptive multilayer model which takes into account an increasing number of layers and achieves a better sensitivity to the refractive index change.

Figure 5:
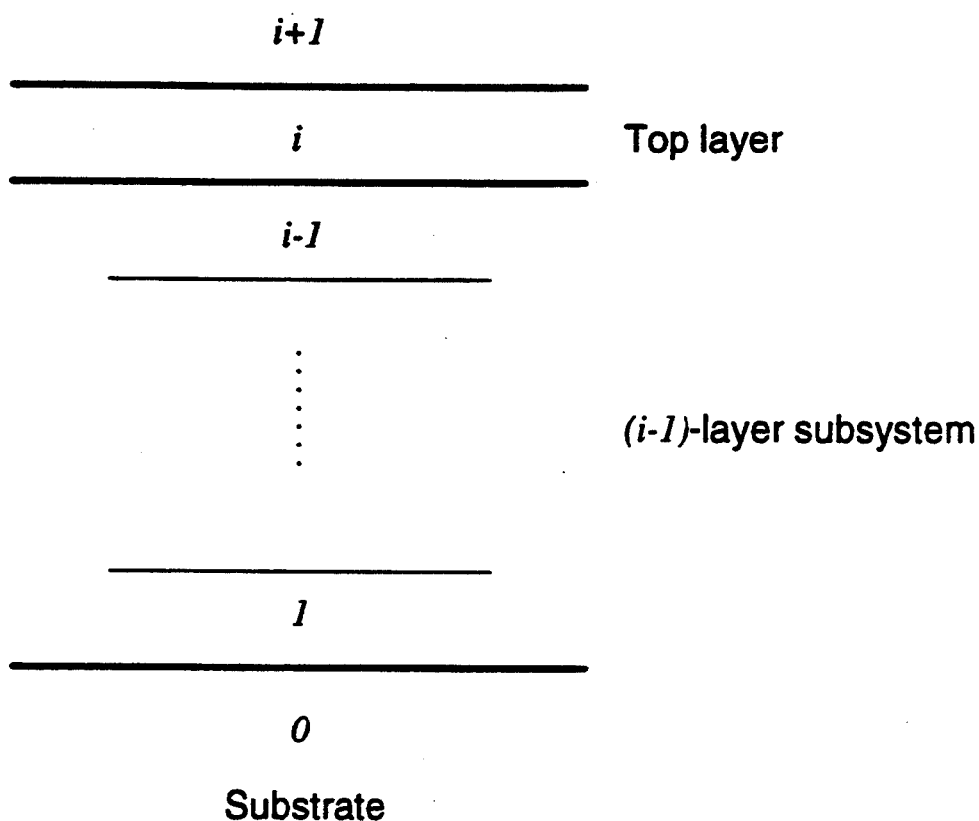
FIG. 5 shows a multilayer thin film system.

The basic formula is based on a well-known recursive calculation of the reflection coefficients of a multilayer system. A given i-layers thin film system ($i \geq 1$), as shown in FIG. 5, can be divided into four parts: the single ith layer on the top of the film stack, a subsystem consisting of all the other i−1 layers beneath it, the ambient or vacuum (the medium i+1, usually with refractive index one), and the substrate (medium 0). The overall reflection coefficient $\Gamma_{i+1,i}$ of the full system measured in medium i+1 is given by $$\overline{r}_{i+1,i} = \frac{r_{i+1,i} + \overline{r}_{i,i-1} X_i}{1 + r_{i+1,i} \overline{r}_{i,i-1} X_i}, \quad i \geq 1, \tag{7}$$

where the unbarred $\Gamma_{i,i-1}$ is the Fresnel reflection coefficient of the interface between medium i and medium i−1 measured in medium i, and $X_i$ is given by $$X_i = exp(-j4\pi n_i d_i \cos\theta_i/\lambda_o), \tag{8}$$

with $\lambda_o$ being the wavelength in vacuum, and $n_i$, $d_i$ and $\theta_i$ being the reactive index, the thickness, and the refraction angle in medium i, respectively. As a new layer is added on top of the stack, the new overall reflection coefficient is easily obtained by the above recursive relation with the initial value $\Gamma_{1,0}=\Gamma_{1,0}$ for i=1. Note that a three-medium model (i=1) with no overlayer is the simplest case of a multilayer system. Hence the computer program for the basic three-medium model is applicable only with some minor modifications.

The adaptive multilayer algorithm assumes that the deposited film, possibly with an arbitrary profile for its refractive index, is a stratified thin film system with increasing number of layers as the thickness of the deposited film increases. The currently deposited layer (i.e., the top layer of the film system) is the only layer with unknown thickness and refractive index, while all the other layers have known optical constants film the previous measurements. Therefore, each measurement will only measure the top layer based on the history of the deposition.

Figure 4B:
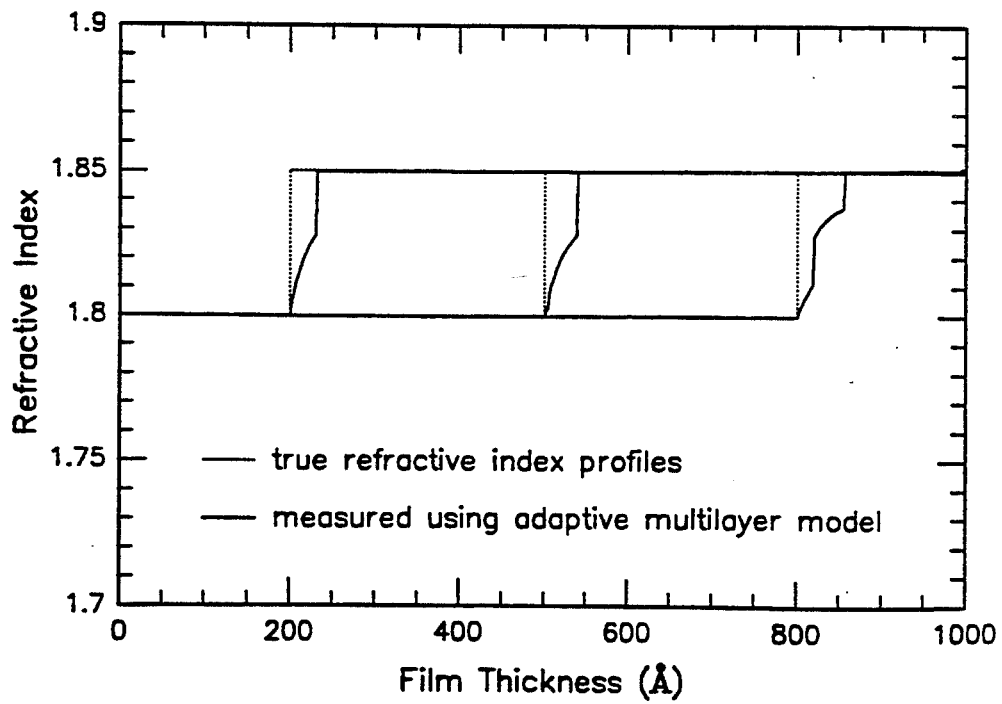
Figure 6:
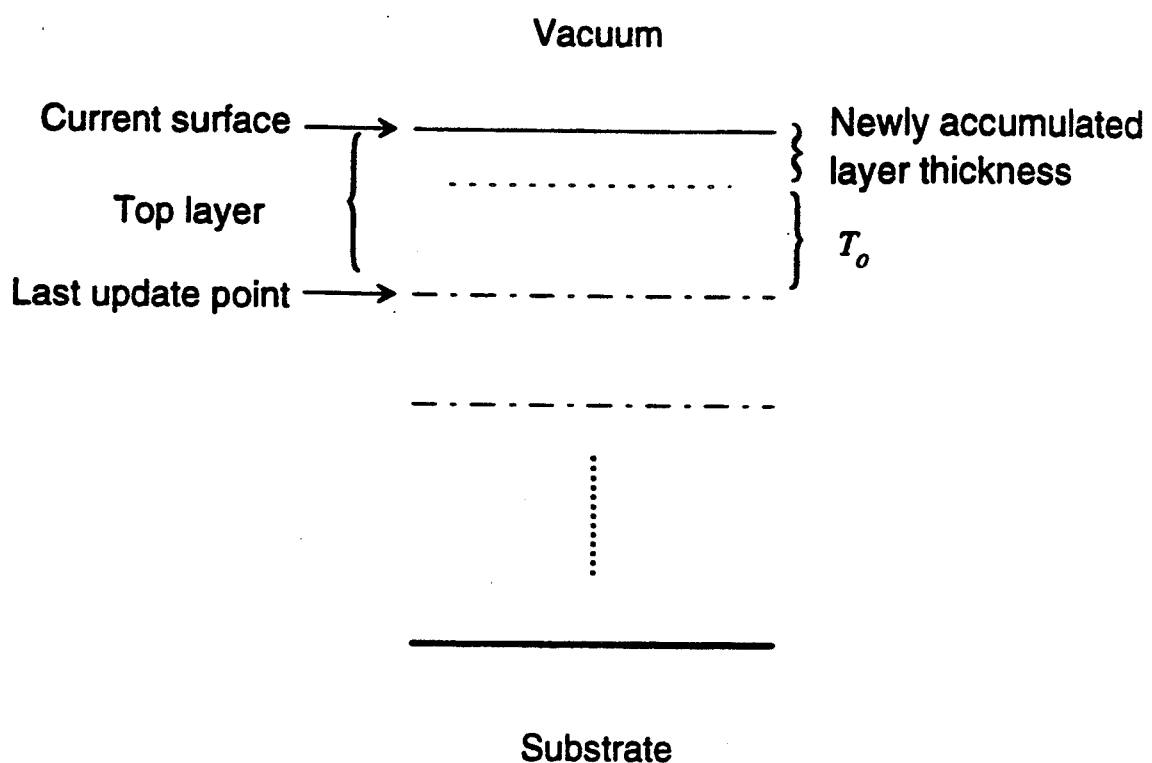
FIG. 6 shows the delayed update scheme of the adaptive multilayer model.

There are different ways to partition the film. For example, one can consider each measurement as a new layer and update the structure of the multilayer system for each measurement, or stack a new layer only when the film thickness reaches some preset limit. Although it appears that it would be better to update the multilayer model as often as possible to keep track of the refractive index variation, in practice it is impractical to do so because an ultra thin film can lead to large measurement errors. Therefore, a minimum updated thickness $T_o$ is selected in the monitoring program. The actual update point in the program is kept until a newly accumulated film thickness $T_o$ is deposited, as presented in FIG. 6. When the newly deposited thickness reaches $T_o$, the previously measured layer of thickness $T_o$ is stacked on top of the subsystem, while the film parameters of the currently deposited layer are saved for the next update. The measurements are then based on the updated subsystem with a film thickness between $T_o$ and $2T_o$. In this way (except at the beginning of a deposition) each measurement measures a layer with a thickness always larger than or equal to $T_o$, and therefore the measurement is not very sensitive to noise. By using the proposed scheme, the sensitivity is greatly improved. This is shown in FIG. 4b, where the same refractive index profiles as in FIG. 4a are measured while using the adaptive multilayer model with $T_o=35$Å. Typically, the model can extract the true index within 50 Å.

The adaptive multilayer model is more sensitive to refractive index changes than the averaged film approach. On the other hand, the averaged film approach provides a convenient way to measure the averaged refractive index of the deposited film. Since, the ultimate goal of the deposition process is to obtain a film with an average pre-selected value of the index, the averaged film approach is used to ensure that this average value of the index is obtained. At the same time, the adaptive multilayer model is used to ensure that the deviation of the film index from the selected average value is minimal and to improve the control response. Both the averaged refractive index and the instantaneous one are displayed on a computer monitor during a coating process.

A total measurement time of 0.5 second is required for extracting the two index-thickness sets of measurements using an IBM compatible 286 PC with a math-coprocessor running at 16 MHz. Further reduction of the measurement time can be obtained by using a faster computer and a higher speed rotating analyzer.

By taking data over one complete revolution of the analyzer, the precision on $\psi$ and $\Delta$ is evaluated to be within 0.1° and 0.15°, respectively, for repeated realignments of the sample holder. This corresponds to a precision of 0.005 and 5 Å on the refractive index and the thickness of an 800 Å $SiO_2$ film on Si. It is found that the precision is not significantly changed over an extended period of time (more than one month). Therefore, system calibration is not required for each new sample. However, remounting the cell windows will cause significant change for the window parameters u and v, and a recalibration is required.

D. Deposition Controls

The total pressure inside the chamber is controlled by an automatic pressure control unit incorporating a servo controlled leak valve to allow oxygen bleeding into the deposition chamber. The deposition rate is regulated by a feedback control unit taking input either from a crystal thickness monitor or from the ellipsometer. The ellipsometer is found somewhat inconvenient for controlling the evaporation rate since it gave a reading only when the shutter is opened to allow deposition on the sample. On the other hand, the crystal thickness monitor is mounted in a position such that the evaporated material is not blocked by the shutter. Hence the crystal thickness monitor allowed the continuous monitoring of the deposition rate, even during shutter closure.

The actual pressure around the sample can be different from that measured by an ion gauge located near the bottom of the chamber. It is also dependent on the position of the leak valve where oxygen is injected. It is found that the stability of the feedback controls for the pressure and the deposition rate (and the change of the associated refractive index of the deposited film) are related to the relative locations of the ion gauge and the leak valve. Several configurations are tested. The best results are obtained when the leak valve is placed at the top of the chamber near the sample, as shown in FIG. 1.

The feedback control of the oxygen flow required for the refractive index adjustment is accomplished by sending a control voltage $V_{ref}$, which is a function of the desired reference pressure $P_{ref}$, from the PC to the automatic pressure control unit which controls the total pressure inside the chamber according to $V_{ref}$. A typical relation between $V_{ref}$ and $P_{ref}$ is given by $$V_{ref} = \alpha \log P_{ref} + \beta \quad (9) \text{ ps}$$

where $\alpha$ and $\beta$ are the circuit parameters of the automatic pressure control unit. The amount of correction to the control voltage, $\delta V_{ref}$, is adjusted according to the refractive index errors given by $$\delta V_{ref} = A_{ave} \delta n_{ave} + A_{ins} \delta n_{ins} \quad (10)$$

where $\delta n_{ave}$ is the error between the targeted refractive index and the averaged index calculated by the four-medium model, $\delta n_{ins}$ is the error between the targeted reactive index and the instantaneous index calculated by the adaptive multilayer model, and $A_{ave}$ and $A_{ins}$ are the feedback coefficients for the two index errors, respectively. To ensure that the control is mostly based on the averaged refractive index, the ratio $A_{ave}/A_{ins}$ is typically chosen larger than one. This also allows a larger excursion of the instantaneous reactive index around the targeted one than the one allowed for the averaged index in order to compensate for error in the average refractive index. In our application, $A_{ave}/A_{ins}=2$ is used. The actual values of $A_{ave}$ and $A_{ins}$ can be roughly calculated from the desired time response and the relation between the deposited refractive index and the total pressure, then experimentally fine tuned to achieve a stable condition. $V_{ref}$ is further limited by upper and lower bounds to prevent unreasonable values that might lead to unstabilities.

The value of the instantaneous refractive index is usually noisy, since a thickness of only 50 Å is used. Because of accumulation of the measurement errors when using the adaptive multilayer model, it is observed that the model might not converge to a solution when the total film thickness reaches a value larger than one quarter wavelength. The averaged refractive index is then the only parameter used for the feedback control.

Experimentally, it is found that sometimes to control both the deposition rate and the chamber pressure at a stable point is difficult. The SiO source would occasionally sublime at an uncontrollable rate, causing an unstable deposition rate and changing the refractive index of the deposited film. In some instances, the oxygen-absorbing capability of the SiO vapor would cause for fluctuation of the chamber pressure as the oxygen flowed. When such an unstable condition developed, the pressure feedback loop for the reactive index control is opened and replaced by a manual adjustment.

The actual optimum thickness for a given diode is related to the type of the laser diode and the refractive index profile of the deposited film. Therefore, the required thickness might slightly vary for different deposition runs. The final point to stop the deposition is accomplished by monitoring the operation characteristics of the laser diode being coated, such as the optical power, the forward bias voltage, or the optical spectrum. For example, in the case of monitoring the optical power, the setup consists of a pulsed current source to drive the laser above the original threshold, and an optical power meter to monitor the laser output power during the deposition. The deposition is stopped when the peak output power decreased to a minimum value. This is the point where the facet reflectivity reached a minimum value.

E. Experimental Results

For each deposition, the chamber is pumped down to a pressure below $5 \times 10^{-7}$ torr. After preheating the SiO source, oxygen is introduced to reach a pre-selected pressure setting and the pressure is kept at this value. The deposition rate is then adjusted to the desired value (about 2~3 Å/s). As the rate stabilized, the shutter is opened to begin the deposition.

Figure 7:
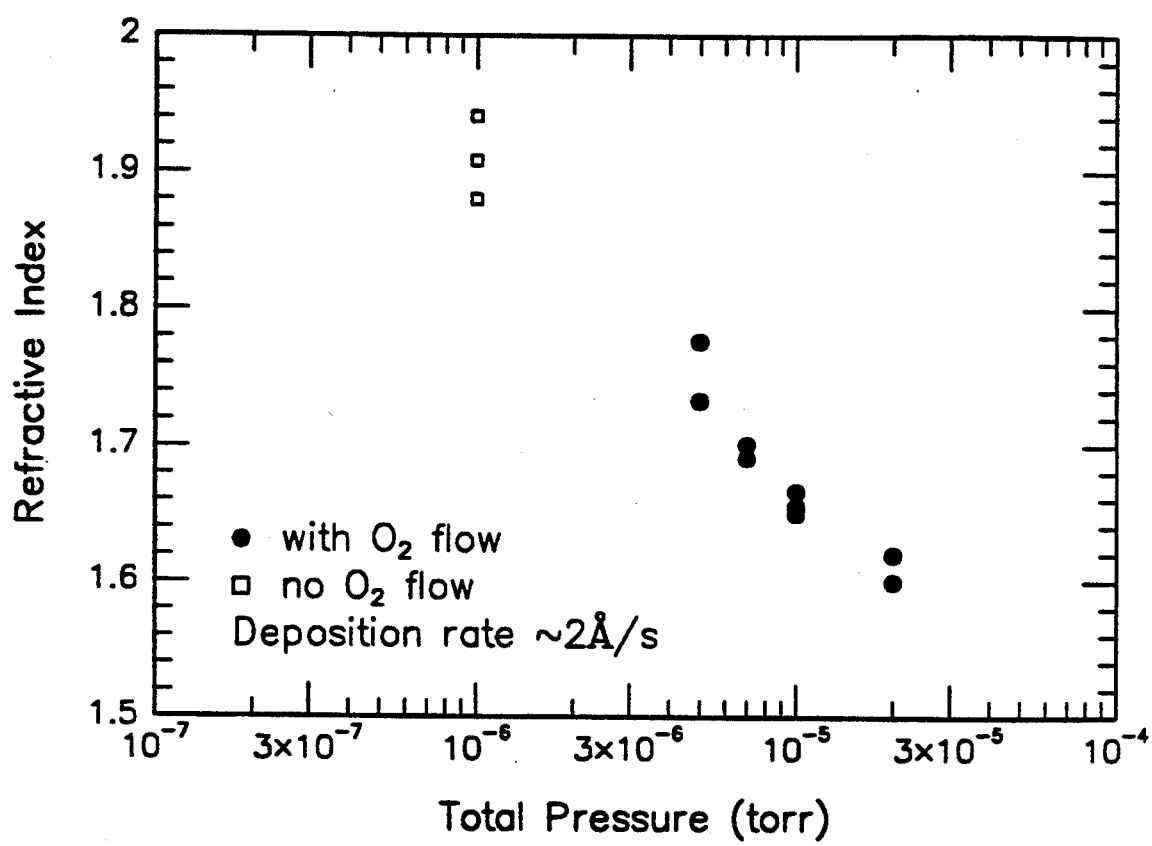
FIG. 7 shows the refractive index as a function of the total pressure.

The relation between the deposited refractive index and the chamber pressure is investigated in a series of calibration measurement, as shown in FIG. 7. All the films are deposited on GaAs wafers with polished surfaces. Before coating, the wafer is cleaned with a standard clean room procedure using TCE, acetone, and methanol, without chemical treatment of the surface. A typical overlayer of 30–50Å is measured prior to a deposition and taken into account in the measurement.

The evaporation pressure of SiO without oxygen flow is measured to be about $1 \times 10^{-6}$ torr. The refractive index of the film could be adjusted from 1.9 down to 1.6 by increasing the total chamber pressure up to $2 \times 10^{-5}$ torr by flowing oxygen. An approximate straight line can be drawn by fitting the data points in FIG. 7. The slope of the line can be used in determining the feedback coefficients $A_{ave}$ and $A_{ins}$.

The data are taken from different runs with no refractive index control during evaporation. With the same initial pressure but no refractive index control, the refractive index of the deposited film is found to be scattered in a range of about 0.1 from run to run. With the real-time ellipsometric monitoring, it is possible to compensate in real time for most variations so that the deposition process had a higher tolerance to such deposition fluctuations. Since the pressure measurement and the oxygen distribution are system dependent, as discussed in Section D, the results shown in FIG. 7 are also system specific.

Figure 8A:
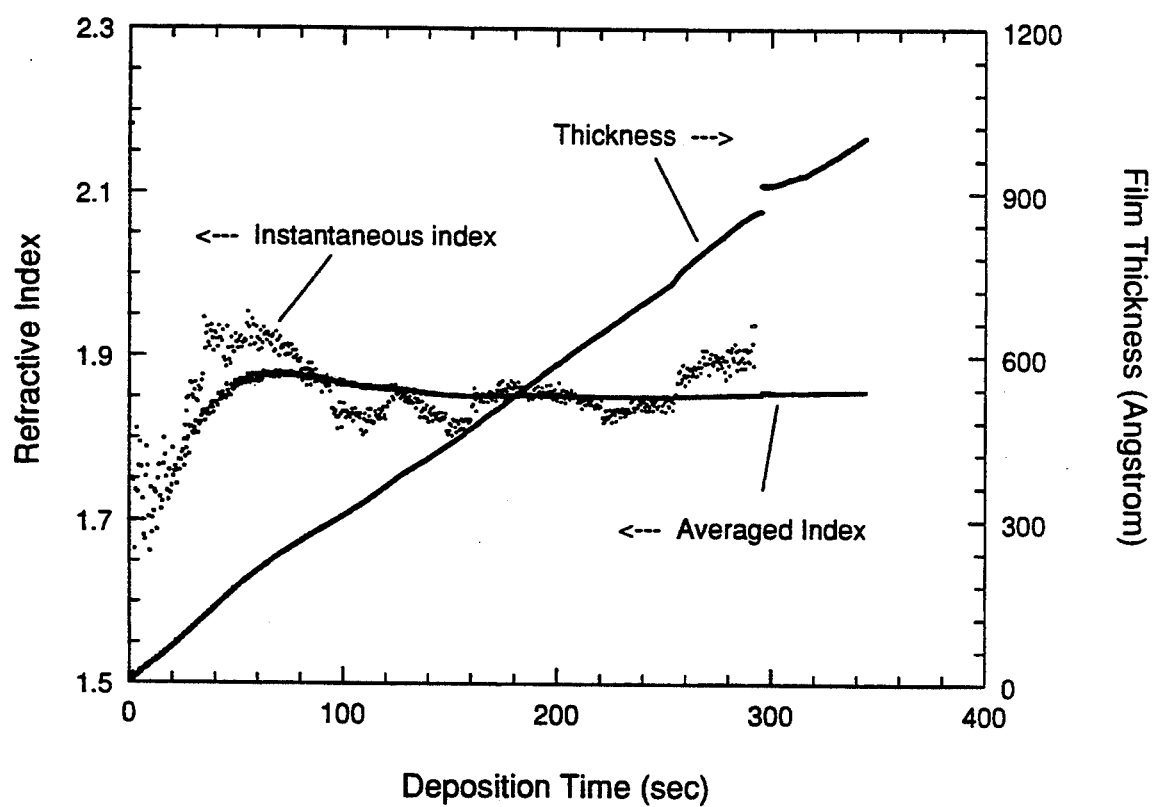
FIG. 8(a): The instantaneous and averaged refractive indices, and the film thickness.
Figure 8B:
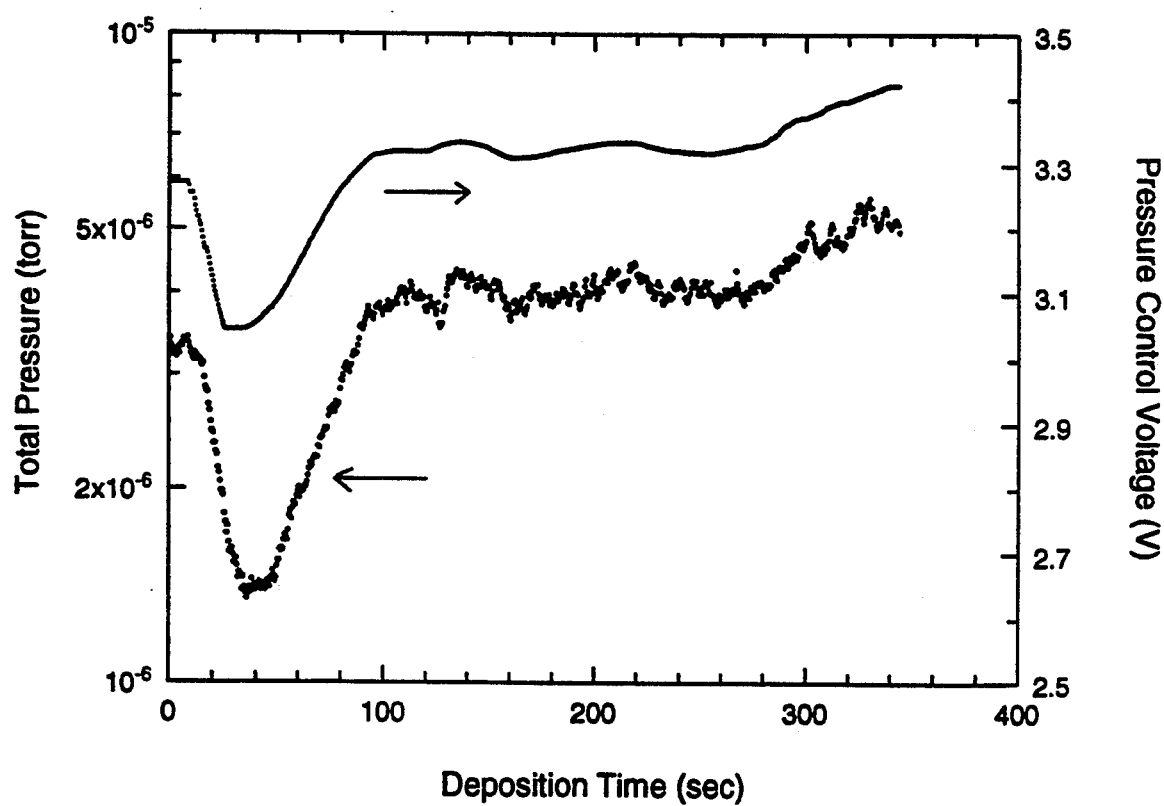
FIG. 8(b): The pressure control signal and the measured total pressure.

For high quality AR coatings, the refractive index control has to be within ±0.02. Initially, the chamber pressure and the deposition rate are set to the approximate values required to reach the desired refractive index value shown in FIG. 7. After the deposition is started, the actual refractive index might slightly deviated from the targeted value. The control process consisted in bringing the reactive index to the desired value by fine tuning the oxygen pressure. FIG. 8 shows a typical experimental run, where an averaged refractive refractive index of 1.85 is targeted within ±0.01. The minimum updated thickness $T_o$ is set to 35Å. FIG. 8a shows the refractive indices measured by the four-medium model and the adaptive multilayer model, and the film thickness from the four-medium model. FIG. 8b shows the corresponding variation of the controlling signal $V_{ref}$ and the measured total pressure. It can be seen that the refractive index of the film measured by the four-medium model is adjusted from 1.75 up to 1.856.

At the beginning of a deposition, the refractive index is subject to large variation due to measurement noises, primarily from the mechanical vibration from the pumps. Large variations in the value of the refractive index are expected since a very thin film is initially measured. The large fluctuations are found to die out quickly as the film thickness increased. The automatic refractive index control loop is not in effect until the initial index fluctuation stabilized at a thickness of about 50 Å. As the film thickness increased beyond a quarter wavelength thickness, the adaptive multilayer model is often found not to converge, and then only the averaged refractive index is used for control. It is important to realize that when the film thickness is comparable to et quarter wavelength, it is already close to the desired thickness and any minor variation of the instantaneous refractive index does not significantly contribute to the averaged refractive index. Therefore, it is acceptable to control only the averaged index. Although the deposition rate is intended to be kept constant, is observed that the deposition rate is slightly affected by small variations of the chamber pressure.

As the film thickness increased and approached a quarter wavelength($\sim$900Å), the reflected light from the sample approached a linear polarization, i.e., $\sin\Delta \approx 0$, and the first order approximation of the small-retardation-waveplate approximation for the cell window is no longer valid. Large errors in the derived thickness and refractive index are then expected around this thickness. A discontinuity in the derived thickness curve can be observed in FIG. 8a. However, the corresponding discontinuity in the film index is less than 0.003, which indicates 1;hat the film index is not sensitive to this error. The thickness error causes no problem in practice, since the final thickness of the deposited film is determined by the minimum optical output of the laser diode being coated.

Figure 9:
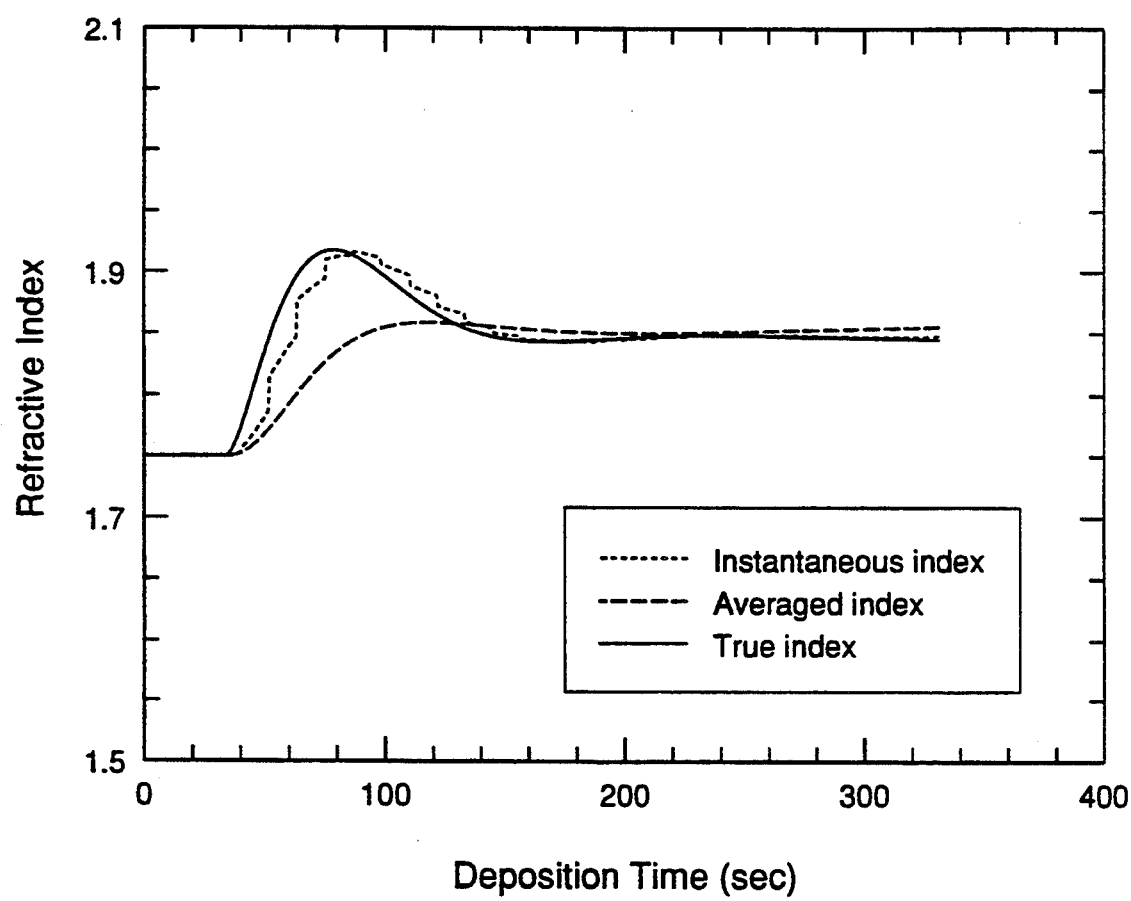
FIG. 9 shows simulated refractive index profiles of a typical deposition process.
Figure 10:
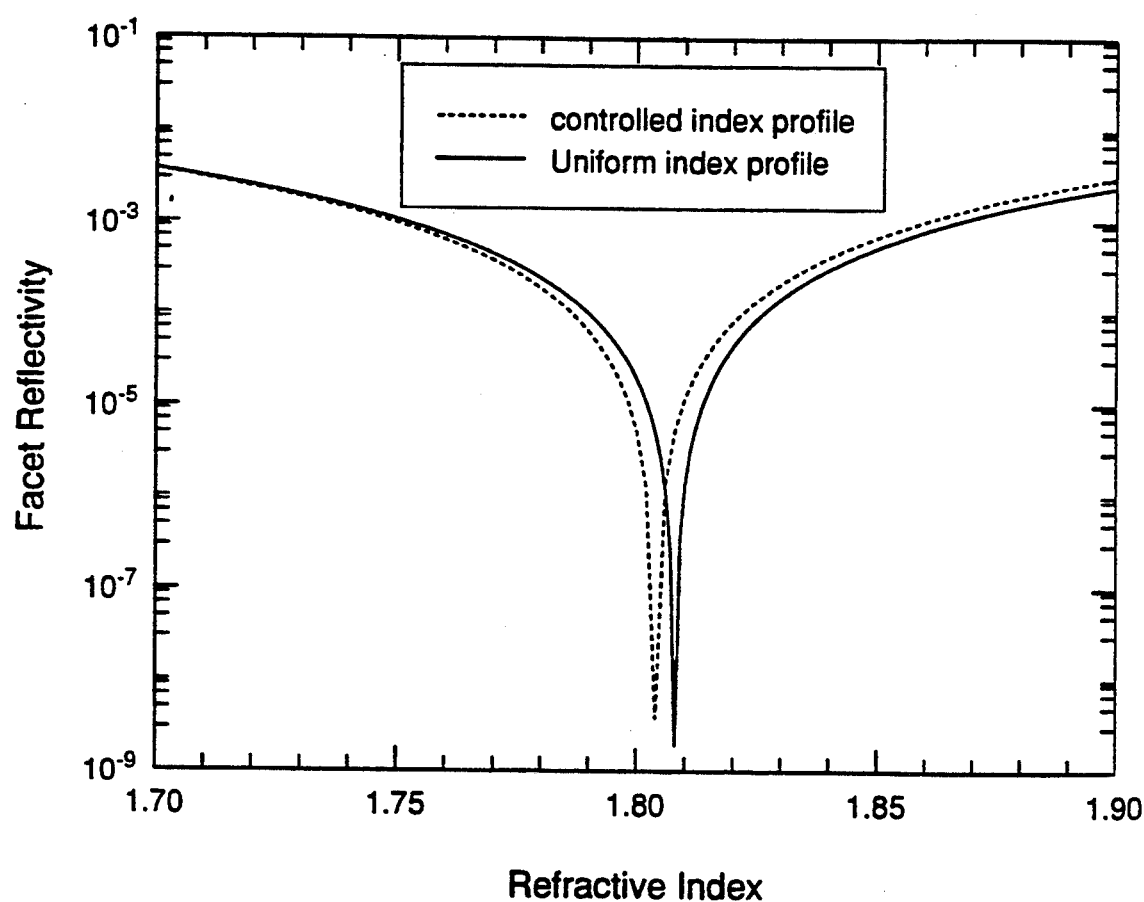
FIG. 10 shows the minimum reflectivity vs. refractive index for a uniform index profile and a controlled nonuniform index profile.

At the beginning of a run, the instantaneous refractive index typically can vary appreciably in order to compensate for the initial index error as shown in FIG. 8a. Therefore, a slightly nonuniform refractive index profile is usually obtained. This raises the question about the valid of emphasizing the control of t, he averaged refractive index. A simulation of the deposition process is conducted to address this issue. FIG. 9 shows the true refractive index and the measured refractive indices using the two thin-film models for a simulated coating process which resembles the experimental data shown in FIG. 8. An initial film of thickness 100 Å (including the initial overlayer) and a refractive index of 1.75 is assumed before the feedback control of the refractive index is 1, turned on. The targeted refractive index is 1.85, and the deposition rate is 3 Å/s with a measurement Lime of 0.5s per data point. It can be seen that due to 1;he nonuniform index profile, the measured averaged index is slightly dependent on the thickness. This results in a slightly sloped profile for the refractive index as the thickness approaches a quarter wavelength. Therefore, the probing wavelength of the RAE should be close 1;o that of the laser diode being coated in order to prevent large index deviation. If such a film is applied to a laser facet, the optimum thickness can be obtained when the calculated reflectivity reaches a minimum. By changing the targeted refractive index, the relation between the reflectivity and the targeted refractive index is obtained. This is shown in FIG. 10, where a set of typical parameters for a laser diode is used. The optimum reflectivity for a film with a uniform index profile is also shown in the same figure. It can be seen that both types of index profiles have a very similar shape, and the difference between the optimum indices of the two curves is within 0.005, which indicates that the averaged refractive index is a proper control parameter. Simulation with other initial conditions also shows similar results.

Although the deposition rate can be a control factor, it is found that the dynamical variation of the deposition rate obtained by adjusting the electron emission current tended to cause unstable deposition conditions. Therefore, this scheme is not adopted, and the deposition rate is kept constant in a typical coating run.

Figure 11:
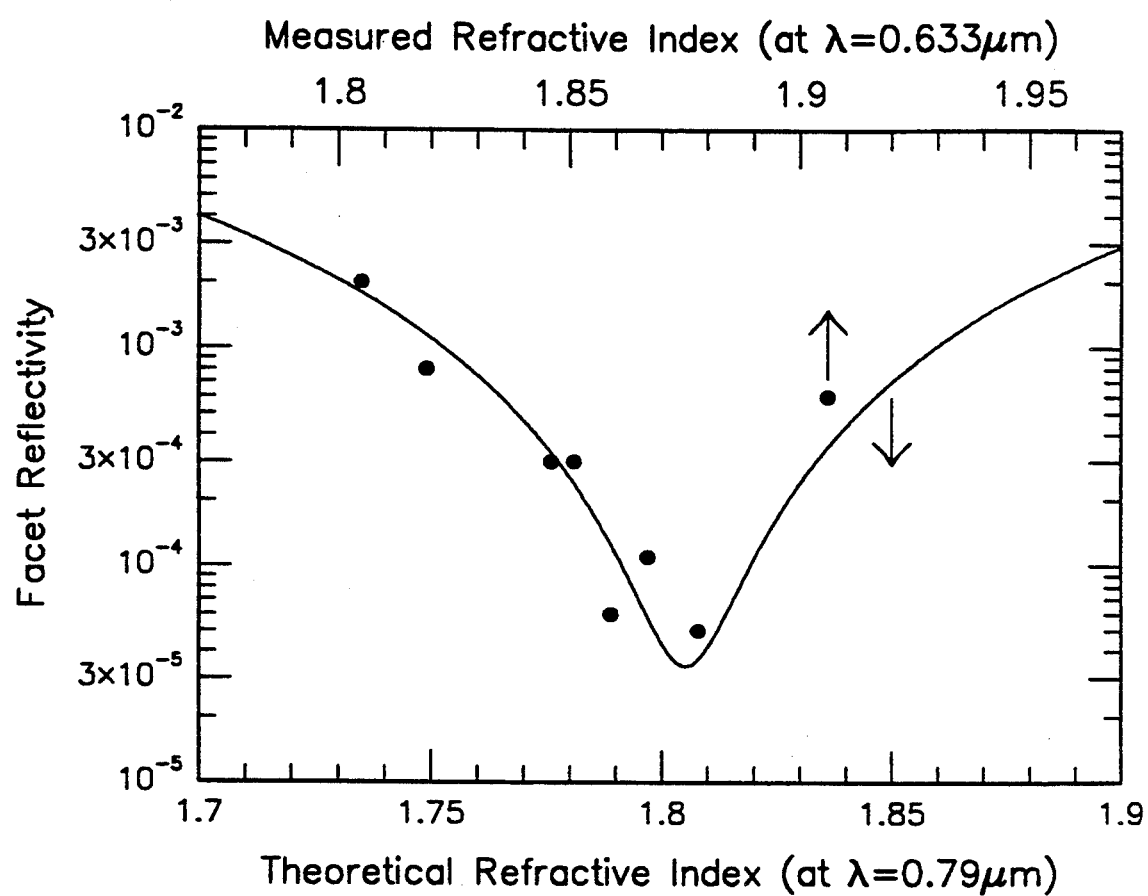
FIG. 11 shows facet reflectivity vs. refractive index. Solid curve: theoretical calculation at the lasing wavelength of the laser diode(lower axis). Dots: measured data at HeNe laser wavelength(upper axis).

The above example demonstrates tile power of in situ ellipsometric monitoring for the control of the averaged refractive index to within ±0.01. Several commercial GaAs CD lasers (PHILIPS part number: CQL21/D) are then AR coated using this approach. The laser half-wavelength passivation coatings are removed prior to coating. Typically, the lasers have a lasing wavelength of 0.79 μm, which is different from that of the HeNe laser used for the ellipsometric measurement. Due to the uncertainties in the value of the dispersion of the refractive index, the true refractive index of tile deposited film at the wavelength of these laser diodes is not precisely known, and in fact is not required for reproducibly coating different lasers. To find the optimum refractive index for the film, different values of refractive indices are deposited, and the corresponding reflectivities are measured. The facet reflectivity is derived from the change of the modulation depths of the spontaneous emission spectra before and after coating. The reflectivity obtained at different refractive index is shown in FIG. 11. The solid curve is the theoretical calculation of the minimal reflectivity at the corresponding refractive index, while the dots are the experimental data. The theoretical calculation has taken into account the slight random variation of the refractive index during the deposition by convolving the calculated reflectivity with a Gaussian distribution of the refractive index with a standard deviation of 0.01. The refractive index difference between the theoretical value (at $\lambda = 0.79/\mu m$) and the measured value (at $\lambda = 0.633 \mu m$) is estimated to be 0.07. By fine tuning the refractive index of the coating, a reflectivity of order $10^{-4}$ or lower is routinely obtained.

F. Passivation Coating Removal for Commercial Lasers

Figure 12A:
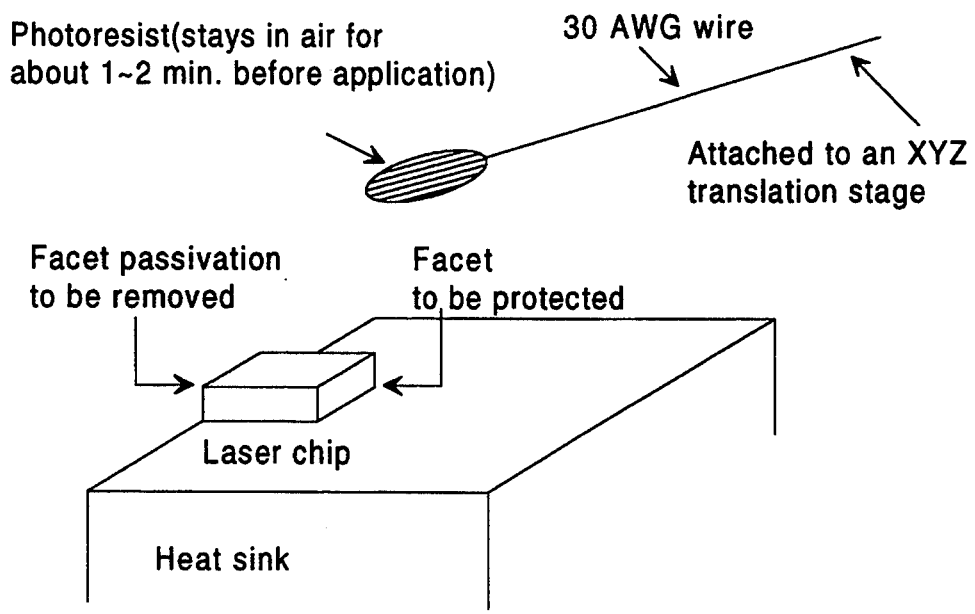
FIG. 12a and FIG. 12b show the application of photoresist on the facet which is not to be affected by the passivation removal procedure.
Figure 12B:
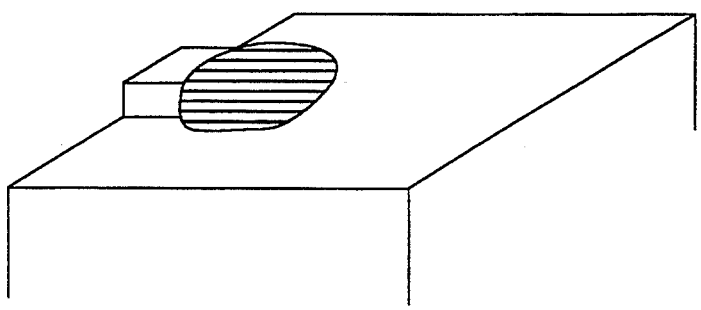

The facets of a commercial laser are typically coated with a half-wavelength layer for passivation. For an AR coating on such facets, the passivation may have to be removed. The removal procedure is described as following:

(1) Apply photoresist to protect the facet which is not to be affected by the removal procedure. Some lasers have different coatings on the two facets. The thickness might be different even though they are intended to be the same. Therefore, each removal procedure should remove only one facet passivation of the laser. To protect the facet which is not to be affected by the removal procedure, a small amount of photoresist is applied to the unaffected facet, as shown in FIG. 12.

(2) Put the laser in a diluted HF solution ($HF:H_2O: = 1:10$) to etch the passivation coating. For a new type of laser with unknown passivation material, frequently (about every 15 sec.) take out the laser, rinse with DI water, blow dry, and check the color of the facet under microscope. Stop etching when the color reaches that of a GaAs substrate. Total about 0.54–4 min. is required, depending on the material of the passivation coating. For known etching rate of the passivation material, frequent checking is only required around the expected finishing time.

(3) Use the ellipsometer to check the etched facet and make sure the passivation has been removed completely. If not, repeat step (2).

(4) Use acetone to remove the photoresist and blow dry.

G. Multilayer Anti-reflection Coatings Without Index Control

The performance of laser amplifiers and broadly tunable external cavity lasers is critically dependent on the ability of depositing ultra-low reflectivity coatings on the laser facets. A multilayer AR coating has several advantages over a single-layer design such as a wider tolerance on the coating parameters or a wider low reflectivity bandwidth. By using a combination of several stoichiometric materials, a multilayer coating is expected to be more stable as compared to a single-layer coating which uses a non-stoichiometric composition. For example, a passivation layer can be added on top of a single AR coating, which typically uses a non-stoichiometric material.

To demonstrate this approach, a double-layer design is considered. Different double-layer coating designs are possible when combining two dielectric materials, one with a refractive index higher than the square root of the substrate index and the other with a lower refractive index. In some circumstances, it is necessary to AR coat commercially available lasers. Typically those lasers have a passivation coating with a thickness of about one half wavelength and a refractive index lower than the square root of the substrate index. A step-down design where the higher index layer is next to the substrate is typically used for a double-layer AR coating. For this configuration, the passivation coating has to be removed. In a step-up design, the passivation coating can be kept and extended to be slightly thicker than one half wavelength. However, the bandwidth of the coating measured at a reflectivity of $10^{-4}$ or less is about one-third of that of a single-layer AR coating.

By using the setup shown in FIG. 1, the original passivation coating parameters (refractive index and thickness of the film) can be measured. Therefore, the required modification to such layer can be obtained by a proper step-up design. For the case of a step-down design, the desired thickness for the first layer can be monitored and controlled by the setup with high accuracy. In both cases, the thickness of the second layer is determined by observing the minimum power of the optical output.

Figure 13:
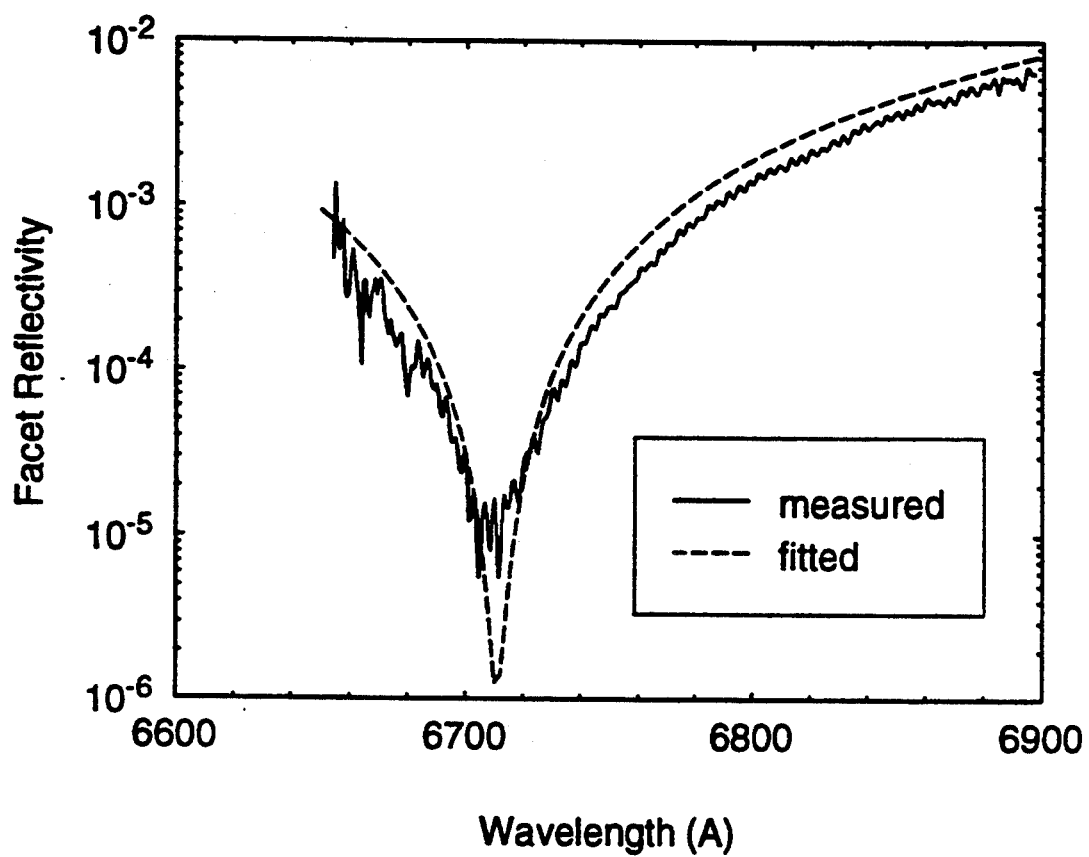
FIG. 13 shows the reflectivity spectra of a step-up $Al_2O_3$(extended passivation)/SiO double-layer coating.
Figure 14:
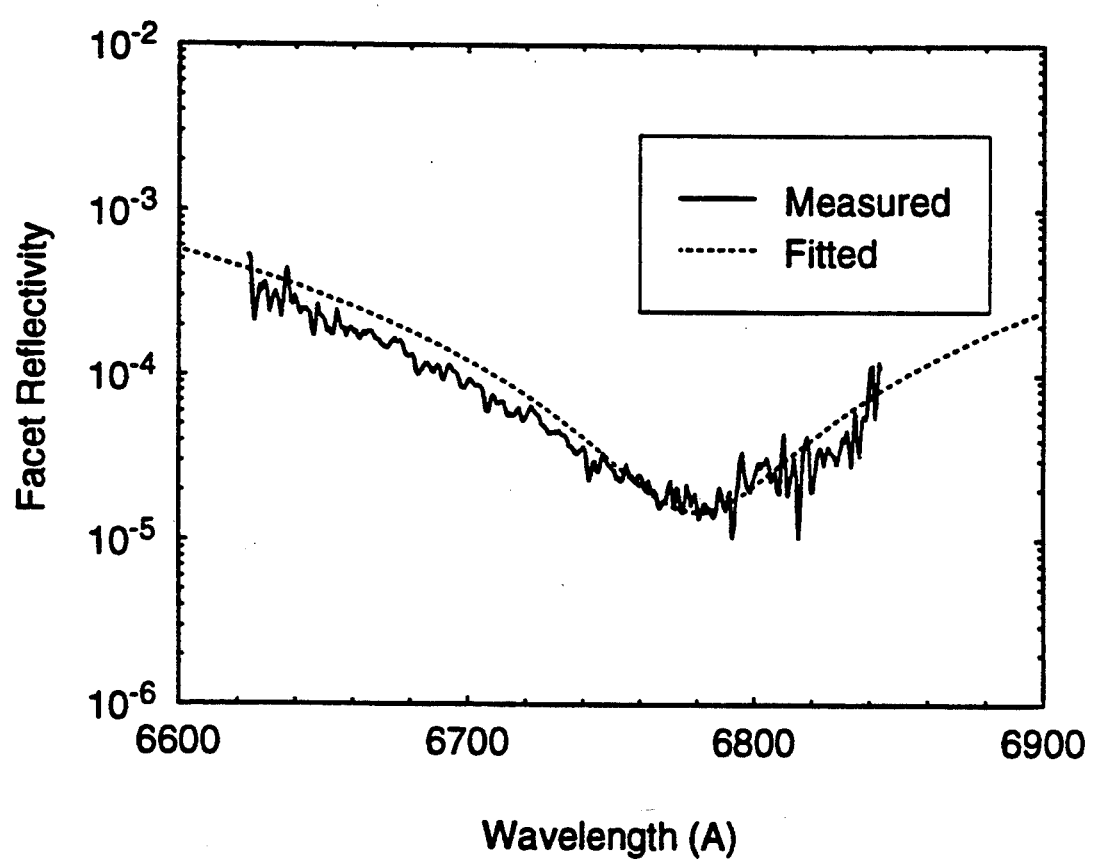
FIG. 14 shows the reflectivity spectra of a step-down $SiO/SiO_2$ double-layer coating (passivation coating removed)

Commercially available visible lasers (Toshiba TOLD9215) are AR coated with and without the original passivation coatings. The original passivation coating, as measured by the ellipsometer, is determined to be $Al_2O_3$ and is less than one half wavelength. This value is thinner than the designed value obtained by simulation. The passivation layer is then extended by depositing additional amount of $Al_2O_3$ to reach the proper value. A second layer of SiO is then deposited. FIG. 13 shows the measured facet reflectivity spectrum(solid line). A theoretical fit using only parameters consistent with the measured ones is also shown(dashed line). A $SiO/SiO_2$ step-down design is also realized by first removing the passivation coating. The measured and fitted facet reflectivity spectra are shown in FIG. 14. Note that the bandwidth of the step-up design with a passivation coating is narrower than the step-down design. Reproducible results with minimum facet refractivities of order $2 \times 10^{-5}$ or less are obtained using both designs for the double-layer coatings.

H. Multilayer Anti-reflection Coatings With Index Control

The technique for index control described in the previous text can be used in a multilayer coating to obtain special coating designs which is difficult when using stoichiometric materials. For example, a double-layer coating can be designed with the first layer coated with the index control scheme while the second layer is a stoichiometric material that acts as a protection layer. The coating can be designed such that the second layer has a large tolerance to compensate for the variation of the refractive index of a, stoichiometric material.

I. Fine-tuning of Anti-reflection Coatings

An AR coating is one kind of optical filter. It is sometimes necessary to fine tune the coating to achieve the best desirable characteristics. This can be done by combining etching and film growth techniques as well as the reflectivity measurement. Basically the reflectivity measurement gives us the wavelength for which the reflectivity is minimum. By removing or adding to the thickness of the film, the wavelength for which the reflectivity is minimum can be adjusted. The amount of thickness to be removed or added can be calculated from the film structure. Wet etching is one of the possible techniques for the film thinning. Another way, which is more convenient and accurate, is to use an ion gun mounted in the deposition chamber shown in FIG. 1. The ion milling process in the chamber can be monitored with the ellipsometer. Other advantages of using the ion gun is that it can be used for in situ sample cleaning before a deposition run and [or ion assisted deposition which provides a denser coating which has more stable film characteristics and is less sensitive to the environmental changes.

OTHER EMBODIMENTS

The invention can use various types well known of deposition techniques, such as thermal evaporation, chemical vapor deposition, sputtering deposition, and molecular beam epitaxy in lieu of electron beam coating techniques as shown in FIG. 1. The wavelength for the measurement should be close to that of the laser being coated. Other types of ellipsometer, such as rotating compensator, rotating polarizer, etc, can be used for the refractive index monitoring, as long as the measurement time for each refractive index should be short enough for effective feedback control. If the refractive index of the deposited film has to be adjusted, material other than SiO, such as TiO, $ZrO_2$, and $SiO_x N_y$ can be used, as long as their refractive index can be changed in a. controllable way. Although the preferred embodiments discussed the removal of the passivation coating on a commercial laser, alternative ways to prepare the device includes actual manufacturing of the required laser diodes without passivation coating, thus not requiring removal of a passivation coating from the facet(s) o[the devices.

The invention thus provides a technique which precisely monitors and controls the averaged refractive index during the deposition of ultra-low reflectivity AR coatings on laser device facets for fabricating laser amplifiers and superluminescent LEDs with high degree of reproducibility.

What is claimed is:

1. In a method of depositing at least one low reflectivity anti-reflection (AR) coating with reflectivity of less than $10^{-3}$ on at least one facet of a laser device using a deposition apparatus that includes a real-time in-situ ellipsometric monitoring means for feedback deposition control of the at least one AR coating, a chamber means for depositing the at least one AR coating, the chamber means includes a pressure leak valve means for controlling an index of refraction of a layer being deposited wherein the at least one AR coating is at least one layer; the improvement comprising the steps of:

(a) preparing the laser device for depositing the at least one layer on at least one facet of the laser device;

(b) preparing a reference means for feedback control of the at least one layer to be deposited by using the ellipsometric monitoring means which monitors an index of refraction and thickness of the at least one layer being deposited;

(c) positioning the reference means and the laser device on a sample holder in the chamber means, the reference means is next to the laser device;

(d) preparing the deposition apparatus for the at least one layer and attaching electrical connections to the laser device whereby the laser device can be electrically excited by an electrical source with an electrical current;

(e) physically aligning the sample holder with respect to the ellipsometric monitoring means such that calibration measurements of an incident angle between the sample holder and the ellipsometric monitoring means can be achieved;

(f) applying the electrical current to the laser device before depositing of the at least one layer begins such that the electrical current is higher than a threshold current of the laser device wherein the threshold current is a minimum current required for the laser device to laser prior to deposition of the at least one AR coating, the electrical current is maintained during the deposition of the at least one layer;

(g) depositing the at least one layer on the at least one facet of the laser device;

(h) using the real-time in-situ ellipsometric monitoring means for measuring ellipsometric angles of $\Delta$ and $\psi$ on the reference means whereby the thickness and index of refraction of the at least one layer being deposited can be determined by a computing means;

(i) using the computing means for evaluating both a calculated i) average and ii) instantaneous indices of refraction of the at least one layer being deposited by inputting to the computing means the monitored ellipsometric angles of $\Delta$ and $\psi$ on the reference means and using derived data from the monitored angles of $\Delta$ and $\psi$ with a non-absorptive deposition model of the at least one layer being deposited whereby the computing means in real-time iteratively solves the calculated i) average and ii) instantaneous indices of refraction of the at least one layer being deposited;

(j) controlling pressure of the chamber means by leaking a gas into the chamber means to change the index of refraction of the at least one layer being deposited to minimize a deposition error signal wherein the error signal is a difference between the calculated i) average and ii) instantaneous indices of refraction of the at least one layer being deposited and a required index of refraction of the at least one layer being deposited; and (k) detecting an operational characteristic of the laser device to determine a deposition end-point of the at least one AR coating on at least one facet of the laser device and stopping the deposition of the at least one layer when the operational characteristic of the laser device is achieved.

2. The method of claim 1 wherein the step of preparing the laser device includes removal of a passivation layer on the at least one facet of the laser device by an etching means wherein the laser device is a commercially available laser device.

3. The method of claim 1 wherein the laser device is a commercially available laser device and the step of preparing the laser device includes measuring a thickness of a passivation layer on at least one facet of the laser device using the ellipsometric monitoring means and partial removal of the passivation layer on the at least one facet of the laser device by etching means whereby the passivation layer forms part of the at least one AR coating.

4. The method of claim 1 wherein the step of preparing the laser device includes selecting a laser device without a passivation layer on the facets of the laser device.

5. The method of claim 1 wherein the step of physically aligning the sample holder with respect to the ellipsometric monitoring means for the calibration of the incident angle is an iterative in-situ calibration technique of a calculated incident angle which minimizes a calculated thickness of a native oxide on the reference means which is derived from the ellipsometric angles of $\Delta$ and $\psi$ on the reference means and information from the non-absorptive model.

6. The method of claim 1 wherein the step of depositing the at least one layer on at least one facet of the laser device is achieved by electron beam deposition.

7. The method of claim 1 wherein the step of using the real-time in-situ ellipsometric monitoring means for monitoring the angles of $\Delta$ and $\psi$ on the reference means are measured with correction of a window effect.

8. The method of claim 1 wherein the step of detecting an operational characteristic of the laser device to determine the deposition end-point of the at least one AR coating includes the use of an optical power photo-detector in the chamber means that monitors a power level from the laser device which causes the at least one AR coating deposition to stop when the power level is a minimum.

9. The method of claim 1 wherein the step of detecting an operational characteristic of the laser device to determine the deposition end-point of the at least one AR coating includes the use of a volt-meter monitoring means attached to the laser device in the chamber means that monitors a forward biased voltage from the laser device which causes the at least one AR coating deposition to stop when the forward biased voltage is at a maximum.

10. The method of claim 1 wherein the step of detecting an operational characteristic of the laser device to determine a deposition end-point of the at least one AR coating includes the use of an optical spectrum analyzer means in the chamber means that monitors a modulation depth of an optical spectrum of the laser device which causes the at least one AR coating deposition to stop when the modulation depth is a minimum.

11. The method of claim 1 wherein the non-absorptive deposition model is a four-medium model which includes a native oxide on the reference means as an initial overlayer and the at least one AR coating to be deposited using the calculated average index of refraction of the at least one layer being deposited.

12. The method of claim 1 wherein the non-absorptive deposition model is an adaptive multi-layer model which divides the at least one AR coating into a multi-layered system that includes using the calculated instantaneous index of refraction of the at least one layer being deposited.

13. The method of claim 1 wherein the error signal generated is a weighted sum of: part i) a difference between the calculated average index of refraction of the at least one layer being deposited and the required index of refraction of the at least one layer being deposited and part ii) a difference between the calculated instantaneous index of refraction and the required index of refraction of the at least one layer being deposited, with a larger weighting applied to the difference of part i) to enhance control of the calculated average index of refraction of the layer being deposited.

14. The method of claim 1 wherein the laser device is a superluminescent diode at completion of deposition of the at least one AR coating on only one facet of the laser device.

15. The method of claim 1 wherein the improvement further comprising the use of a multi-layered design for the at least one AR coating with repeated controlled deposition comprising the steps (a)–(k).

16. The method of claim 1 wherein the improvement in the method further comprising a step of modifying the at least one AR coating by an etching means for removing excessive deposition of the at least one layer.

17. The method of claim 1 wherein the improvement further comprising a repeated controlled deposition on a second facet of the laser device by repeating steps (a)–(k).

18. The method of claim 17 wherein the laser device is a traveling wave laser amplifier at completion of deposition.

19. The method of of claim 1 wherein the improvement in the method further comprising after at least a first controlled deposition of at least one AR coating of the laser device which is a first processed device of a particular make and design wherein the step (k) is required, subsequent laser device processing of the particular make and design comprises the processing steps (a)–(j) without the step of detecting the operational characteristic of the laser device to determine the deposition end-point.

* * * * *